United States Patent [19]
Prewitt et al.

[11] Patent Number: 4,546,438
[45] Date of Patent: Oct. 8, 1985

[54] RHEOMETER AND PROCESS OF CURING AND TESTING RUBBER

[75] Inventors: William T. Prewitt, Tallmadge; James A. Van Dyke, Akron, both of Ohio

[73] Assignee: The Goodyear Tire & Rubber Company, Akron, Ohio

[21] Appl. No.: 536,181

[22] Filed: Sep. 27, 1983

[51] Int. Cl.⁴ .................. G06F 15/46; G01N 3/32
[52] U.S. Cl. .................. 364/473; 73/59; 73/815; 364/476; 374/48; 374/53
[58] Field of Search .......... 364/473, 476, 550, 551, 364/556, 557; 73/59, 770, 811, 814, 815, 841, 843; 374/48, 53, 102–107; 264/40.1–40.7; 425/135, 143, 144, 149, 169

[56] References Cited

U.S. PATENT DOCUMENTS

| | | | |
|---|---|---|---|
| 3,182,494 | 5/1965 | Beatty et al. | 374/48 |
| 3,581,558 | 6/1971 | Porter et al. | 73/811 |
| 3,681,980 | 8/1972 | Decker | 73/811 X |
| 3,688,568 | 9/1972 | Karper et al. | 73/815 X |
| 3,726,132 | 4/1973 | Bibby et al. | 73/770 |
| 3,769,830 | 11/1973 | Porter et al. | 374/48 |
| 3,929,012 | 12/1975 | Anagnostopoulos et al. | 73/815 X |
| 4,095,461 | 6/1978 | Starita | |

OTHER PUBLICATIONS

Monsanto Instruments "Rheometer 100S" Bulletin, 1980.

Primary Examiner—Joseph Ruggiero
Attorney, Agent, or Firm—Charles W. Shifley; T. P. Lewandowski

[57] ABSTRACT

A rheometer and process of curing and testing rubber samples precisely controls each cure and test. The maximum resistance, or more specifically, maximum torque at peak stress, is predicted for each sample automatically as curing progresses. Each cure and test is terminated as soon as maximum resistance is predicted, thereby shortening each cure and test from about one-quarter to one-third.

16 Claims, 3 Drawing Figures

4,546,438

RHEOMETER AND PROCESS OF CURING AND TESTING RUBBER

BACKGROUND OF THE INVENTION

This invention relates to an apparatus and a process for curing and testing rubber.

Rheometers are known to the art of curing and testing rubber. As now known, a rheometer is a device for curing and testing rubber with a heated curing chamber into which raw uncured rubber samples are loaded to be transformed into the different, cured state. Within the heated curing chamber, a small ribbed rotor oscillates in contact with a loaded sample. A strain gauge senses torque upon the rotor caused by resistance of the rubber sample to rotor oscillation. Limit switches activate momentarily at each of the two extremes of rotor oscillation, to indicate the precise moments at which peak stress occurs. A recording device produces a graph of torque at peak stress versus time over the duration of a cure. A human operator observing the graph stops the cure by opening the rheometer and removing the sample. The operator stops the cure after the maximum torque at peak stress is reached and observed. Cure characteristics of the samples, including maximum torque at peak stress, are used for quality assurance of rubber batches from which the samples are taken, compounding error detection, and design of items made of the batches.

Known rheometers are each major investments in the art of rubber curing. As a result, the time taken for each cure and test with a rheometer is a critical factor in the successful commercial use of the rheometer. With rheometers as known, each cure and test must be continued through the time a maximum torque at peak stress is reached and observed. Further, the decision when to terminate a cure and test is undesirably left to the discretion of the operator, who can use only whatever judgment he has, based upon observation of the graph, that the maximum torque has been reached. The necessity of awaiting the achievement of maximum torque at peak stress, and the uncertainty in the decision to terminate the cure and test, results in increased times for cures and tests, and resultant loss of rheometer time for other cures and tests.

SUMMARY OF THE INVENTION

An object of the inventors in making this invention was to provide a precision rheometer apparatus and a precision curing process, for greatly improved and fuller utilization of the rheometer.

Another object was to provide a precision rheometer apparatus, and curing and testing process, which accurately predict maximum torque at peak stress, to make possible the termination of each cure and test before the actual achievement of maximum torque at peak stress.

Thus, in a principal aspect, the invention is a process of curing and testing a rubber sample which begins with the rubber sample being heated. During the heating, a plurality of measurements are made of the resistance of the rubber sample to generate a plurality of resistance measurements and corresponding times. Several characteristics of resistance are then determined from the measurements and corresponding times. A minimum resistance $S_{min}$ is determined. After determination of $S_{min}$, the maximum rate $S_{max}'$ of change of the resistance is determined. From the following resistance measurements, determination is then made of the occurence of a rate of change of the resistance $S_{det}'$ which is approximately a selected ratio to the maximum rate of change $S_{max}'$. Also determined are the resistance, $S_{det}$ at which the rate of change equals $S_{det}'$, and the acceleration $S_{det}''$ of the resistance in proximity to the rate of change $S_{det}'$. An expected maximum resistance Y of the rubber sample during the heating is then predicted, according to the relationship $$Y = S_{det} + (S_{det}'(1 - S_{det}'/(S_{det}'' \times K)))/2$$

where K is a constant. Finally, as soon as the predicted maximum resistance Y is predicted, the cure and test is terminated. The cure and test is not continued through the actual achievement of maximum resistance.

As a result of termination of the cure and test before the actual achievement of maximum resistance, about one quarter to one third of the time of prior art cures and tests is eliminated. Thus, each rheometer used in the cures and tests can be used for about a quarter or third more cures and tests. More curing and testing can be accomplished with the same or fewer rheometers, in the same or less time.

These and other objects, aspects and advantages of the invention are more fully described in the detailed description of the preferred embodiment, which follows a brief description of the drawing.

BRIEF DESCRIPTION OF THE DRAWING

Briefly, the drawing consists of four figures or FIGS.

DETAILED DESCRIPTION OF THE PREFERRED EMBODIMENT

Figure 1:
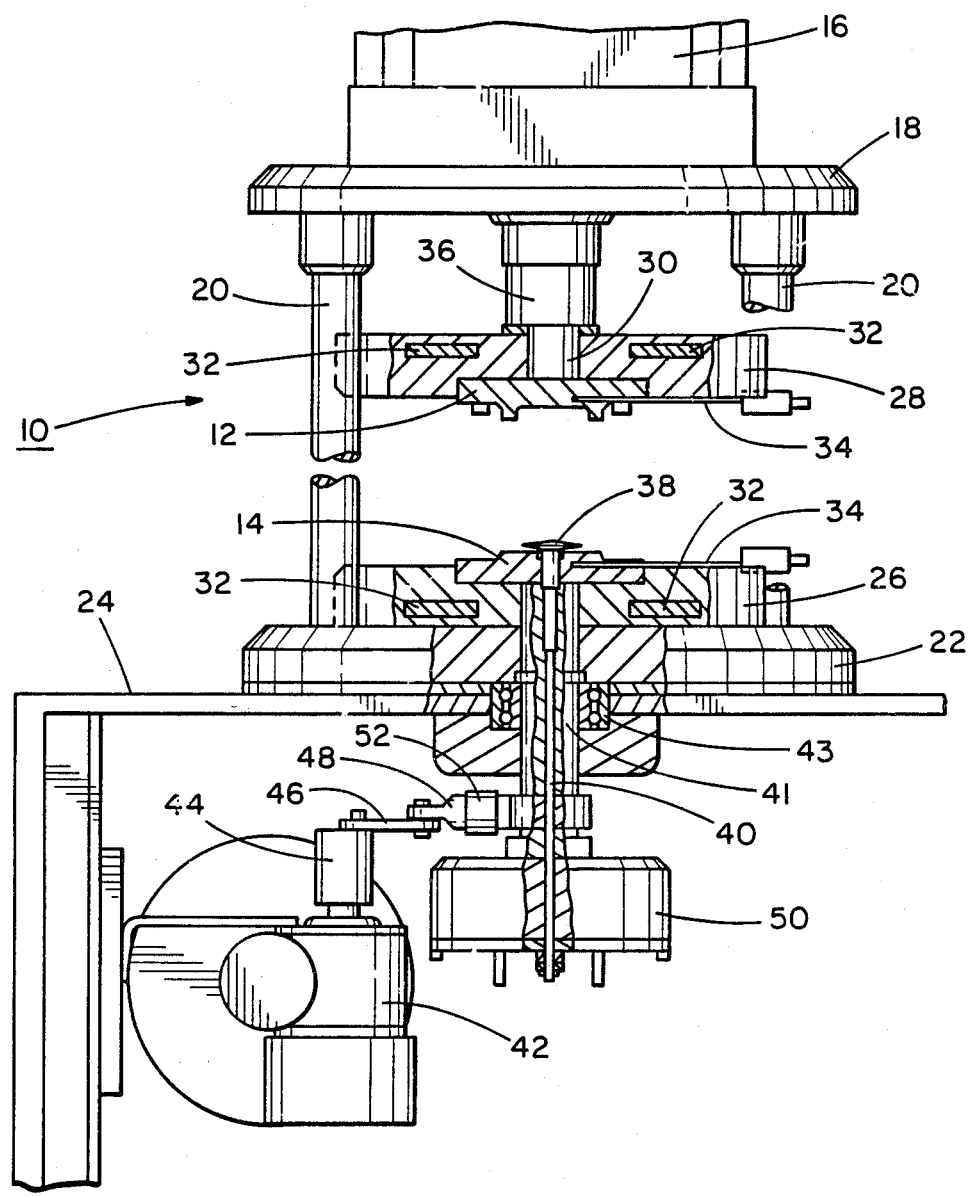
FIG. 1 is a diagrammatic view of a portion of the preferred apparatus of the invention.

Referring to FIG, 1, the preferred apparatus comprises, in part, a rheometer 10 having an upper die 12 and a lower die 14 defining a die cavity for rubber samples (not shown). Samples are successively loaded in the die cavity, which is closed by lowering the upper die 12 through operation of a pneumatic cylinder 16.

The cylinder 16 is supported atop a frame plate 18 and underlying frame rods 20. The rods 20 extend from a rod base 22 atop a base support 24. The lower die 14 rests on a lower heating platen 26, which rests on the base 22. The upper die 12 is mounted to the underside of an upper heating platen 28, which is mounted to the rod 30 of the cylinder 16.

The platens 26, 28 include embedded electrical heaters 32. The dies 12, 14 include heat probes 34. A rod insulator 36 protects the rod 30 from heat.

The heaters 32 heat the platens 26, 28, dies 12, 14 and any sample in the die cavity. The probes 34 provide feedback for accurate control of the heaters 32, and accurate heating of samples.

A biconical disc 38 of a rotor projects into the die cavity. The disc 38 is mounted atop an oscillatory rotor shaft 40, which projects through the lower die 14, lower platen 26, rod base 22 and base support 24. The shaft 40 is rotatably mounted to the base support 24 within a shaft support 41 and bearing 43. The shaft 40 and disc 38 are oscillated by a main, line synchronous motor and gear box 42 mounted to the base support 24. The main motor and gear box 42 drive an eccentric 44. The eccentric 44 rotates, and rotates the attached end of a link arm 46. The other end of the link arm 46 oscillates a torque arm 48 and the shaft 40.

The rotor shaft 40 is pneumatically clamped by a pneumatic clamping mechanism 50. The rotor is oscillated through an arc of a few degrees, preferably at approximately 100 cycles per minute as determined by the motor 42 and gear box. Limit switches 51 (not shown in FIG. 1) respond to the extremes of movement of the link arm 46, to indicate the precise moments at which the link arm and disc 38 reach maximum travel, and thereby the precise moments at which peak stress occurs on a sample.

A torque arm transducer, such as the strain gauge 52, measures the torque upon or strain in the torque arm 48. The strain in the torque arm 48 is representative of, and more specifically, proportional to, the torque upon the arm 48, arising from the resistance of the sample to the oscillation of the rotor. The resistance arises from and increases with cross-linking occurring within the rubber as it cures. Thus, the gauge 52 measures the strain upon the rotor, which is proportional to the torque of the resisting rubber samples. The torque applied to the rotor causes a change in the voltage of the transducer proportional to the torque arising from the sample resisting oscillation of the rotor. The frequency of the torque signal is approximately 100 cycles per minute, corresponding to the frequency of rotor oscillation.

Figure 2:
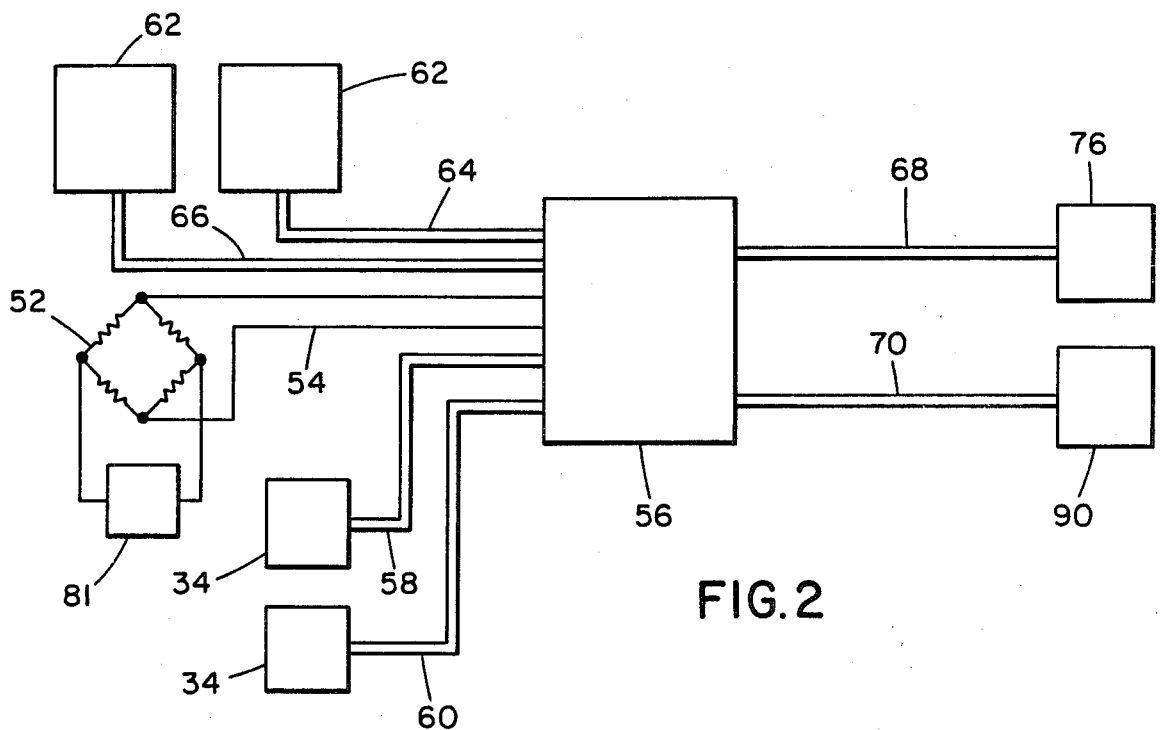
FIG. 2 is a schematic view of the preferred apparatus.

Referring to FIG. 2, the torque or strain signal is transmitted by lines 54 to an electronic central or master controller 56, which includes a digital, microprocessor based central processing unit, storage registers, analog-to-digital converters, and associated hardware. The controller 56 also receives temperature signals from the probes 34 along lines 58, 60, and timing signals from the limit switches 62 along lines 64, 66. The central controller 56 may generate control signals to several slave controllers, including cylinder controller, a heater controller, a motor controller, a clamp controller and a strain gauge controller. As should be apparent, such controllers may include only power supplies, or be significantly more sophisticated. As most preferred, however, the controller 56 controls only a display 76 and a recorder 90 through lines 68, 70.

The controller 56 receives an analog signal from the strain gauges 52 and filters, and converts or intermittently reads the signal to generate a plurality of digital torque signals corresponding to measurements of the torque upon the rotor at peak stress. The controller 56 employs signals from the limit switches 62, of the closing thereof, to recognize the precise moments of peak stress. The controller 56 generates the digital torque signals at these precise moments. The controller 56 then stores and processes the torque measurements as follows.

Figure 3:
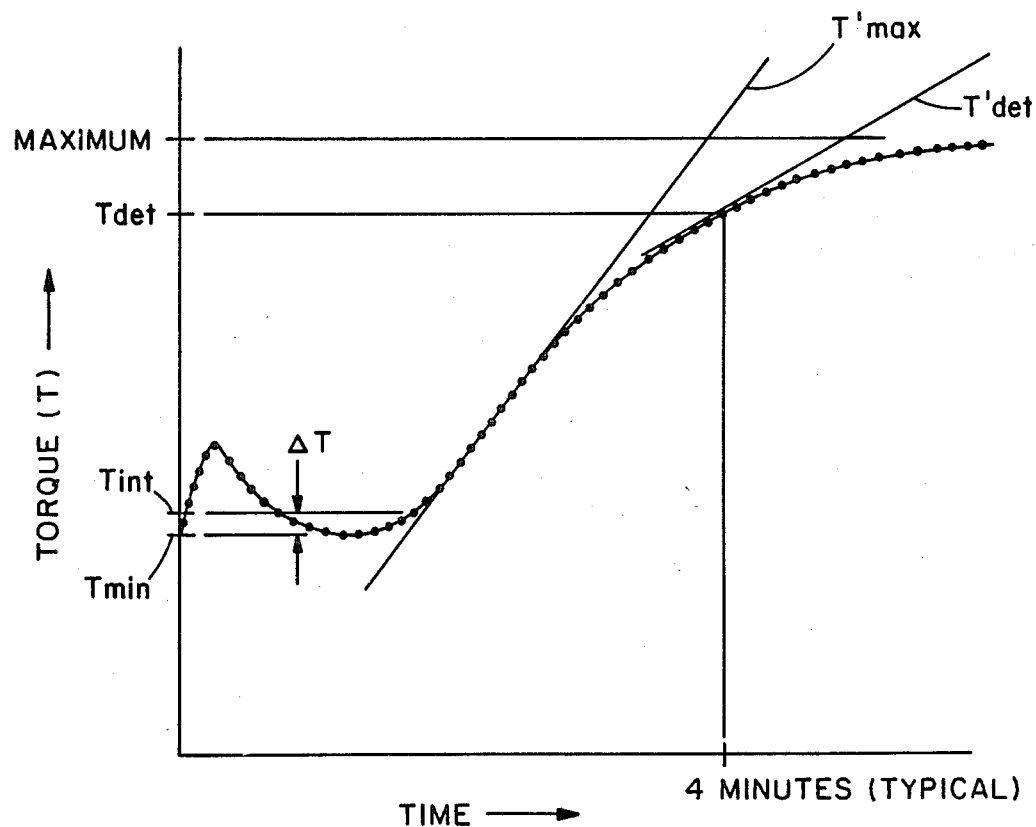
FIG. 3 is a chart of the resistance characteristics of differing rubber samples, for illustration of such characteristics.

Successive torque measurements are "averaged" to generate a plurality of average torque values at peak stress. That is, by definition of "averaging", successive torque measurements are subtracted, and the absolute value of their difference divided by two. As the curing progresses, the average torque values are compared to each other to generate a minimum average torque value, shown by example in FIG. 3 as torque value $T_{min}$.

After the minimum average torque value is recognized, the following average torque values are compared to the minimum average torque value to generate a first selected or intermediate average torque value $T_{int}$ which is a selected amount $\Delta T$ greater than the minimum average torque value. Most preferably, $\Delta T$ equals one deci-newton-meter.

At least several of the average torque values close in time to and following the first selected average torque value $T_{int}$ are then manipulated to generate a maximum first derivative value $T_{max}'$ of the average torque values. Most preferably, beginning at $T_{int}$, and repeating every six-tenths of a second thereafter, the ten most recent average torque values are manipulated to obtain a first derivative value T'. This first derivative value is compared to the maximum of any previously obtained first derivative values. If the new first derivative value exceeds the maximum of the previously obtained first derivative values, or is the first such value, the new value is adopted as the maximum of the first derivative values. If the maximum of the first derivative values remains unchanged for ten consecutive comparison cycles, it is declared to be the maximum first derivative value $T_{max}'$ for the test.

From the maximum first derivative value $T_{max}'$, a first derivative value $T_{det}'$ is determined, $T_{det}'$ being approximately of a selected ratio to $T_{max}'$. Again as most preferred, the ratio R of $T_{det}'$ to $T_{max}'$ is 0.25. $T_{det}'$ is most preferably determined as follows. First, from $T_{max}'$, a target first derivative value $T_{tar}'$ is calculated, according to the equation $T_{tar}' = R \times T_{max}'$. First derivative values are generated following $T_{max}'$ and compared to $T_{tar}'$. The first of the first derivative values found to be less than $T_{tar}'$ is declared to be $T_{det}'$, and the average torque value corresponding to the selected first derivative value $T_{det}'$ is declared to be a second selected average torque value $T_{det}$.

The average torque values close in time to the second selected torque value $T_{det}$ are then manipulated, to generate the second derivative $T_{det}''$ of the average torque values at the second selected average torque value $T_{det}$. As most preferred, the second derivative is determined from examination of the twenty average torque values prior to value $T_{det}$.

At this stage, the controller 56 will have stored values of $T_{det}$, $T_{det}'$, $T_{det}''$ and an acceleration scale factor K. Most preferably, the controller 56 will have stored a full array of the average torque values. With the preferred 0.25 ratio identified above, and the stated sampling interval of 0.6 seconds, K equals 0.45 for best results. The controller uses these stored values of $T_{det}$, $T_{det}'$, $T_{det}''$ and K in a calculated prediction of the maximum torque at peak stress expected in the curing of the rubber sample. The predicted maximum torque is designated Y, and calculated according to the formula $$Y = T_{det} + (T_{det}'(1 - T_{det}'/(T_{det}'' \times K)))/2$$

Once the predicted maximum torque Y is predicted, the controller 56 may search the array for, or calculate, through conventional and known relationships, the percentage cure parameters, a cure rate, and cure amount (max−min) for the sample. The controller may compare such calculated values to predetermined, acceptable values, and grade the test and cure as acceptable or unacceptable. Most preferably, the prediction of maximum torque Y is updated as new average torque values are generated, for greater ratios of selected first derivatives of average torque values to the maximum first derivative value. Such updating continues, as most preferred, until the current average torque value reaches ninety percent of the predicted maximum Y. Percentage cure parameters and the rest are then calculated. Updating as described is preferred to assure a ninety percent cure parameter is a measured value, as opposed to a calculated value.

As soon as the predicted maximum torque Y is known and updated as desired, the controller 56 or most preferably, an operator, may either terminate the heating and rotor oscillation, de-energize the limit switches and strain gauge, and open the sample die cavity, or remove the tested sample and insert another. In either event the cure and test for which Y has been predicted may be terminated. A recorder 90 may record the data created by the cure and test.

The invention, and the manner and process of making and using it, are now described in such full, clear, concise and exact terms as to enable any person skilled in the art to which it pertains, to make and use the same. It is to be understood, of course, that the forgoing describes a preferred embodiment of the present invention and that modifications may be made therein without departing from the spirit or scope of the present invention as set forth in the claims. As an example, other prediction equations may be used which relate current torque, the first and second derivatives of current torque versus time, and prior values, to yield expected values of torque at which the first derivative of torque is zero. To particularly point out and distinctly claim the subject matter regarded as invention, the following claims conclude this specification.

We regard as invention and claim:

1. A process of curing and testing a rubber sample comprising:
   (a) heating the rubber sample;
   (b) making at least a plurality of measurements of the resistances of the rubber sample during heating, to generate a plurality of resistance measurements;
   (c) determining, from the resistance measurements, a minimum resistance $S_{min}$;
   (d) determining, following $S_{min}$ and from the resistance measurements, the maximum $S_{max}'$ of change of the resistance;
   (e) determining, from the resistance measurements, the occurence of a rate of change of the resistance $S_{det}'$ of approximately a selected ratio to the maximum rate of change $S_{max}'$;
   (f) determining, from the resistance measurements, the resistance $S_{det}$ at which the rate of change equals $S_{det}'$;
   (g) determining, from the resistance measurements, the rate of change $S_{det}''$ of the rate of change of the resistance in proximity to the rate of change $S_{det}'$;
   (h) predicting an expected maximum resistance Y of the rubber sample during the heating according to the relationship $$Y = S_{det} + (S_{det}'(1 - S_{det}'/(S_{det}'' \times K)))/2$$

where K is a constant; and
   (i) terminating the test and cure based on the expected maximum resistance Y.

2. The process of claim 1 in which the measurements of the resistance of the rubber sample S are measurements of the resistance of the rubber sample to motion of an oscillating member.

3. The process of claim 2 in which the measurements S are measurements of the torque of the oscillating member.

4. The process of claim 3 in which the measurements are measurements of the torque at peak stress of the oscillating member.

5. The process of claim 1 in which the measurements of resistance are the averages of successive actual measurements of resistance, and in which the actual measurements are made approximately 200 times per minute.

6. The process of claim 1 further comprising, before step (d), the step of determining an intermediate resistance $S_{int}$ which is a selected amount $\Delta S$ from the minimum resistance $S_{min}$, and in which the step (d) begins following the determination of the intermediate resistance $S_{int}$.

7. The process of claim 1 in which the selected ratio of $S_{det}'$ to $S_{max}'$ is 0.25.

8. A process as in claim 1 in which the steps (e) through (h) are performed repetitively, once each for a plurality of selected ratios of the rate of change of the resistance $S_{det}'$ to the maximum rate of change $S_{max}'$.

9. A process as in claim 1 in which the curing and testing of the sample is terminated before the resistance measurements correspond to the expected maximum resistance.

10. A process as in claim 1 in which the heating is performed in a heated curing chamber.

11. A process as in claim 1 in which the steps (c) through (i) are performed by digital analysis of the resistance measurements.

12. A process as in claim 1 in which the steps (c) through (i) are performed by analog methods.

13. A process of successively curing and testing rubber samples comprising:
   (a) loading the samples successively into a rheometer having a heated curing chamber for the samples, an oscillating rotor for testing the resistance of the samples to motion of the rotor, limit switches for repetitively indicating the precise moments of peak stress on the sample, at least one strain gauge for sensing torque upon the rotor caused by resistance of the rubber samples to motion of the rotor;
   (b) heating each rubber sample in the curing chamber;
   (c) oscillating the rotor and energizing the limit switches and strain gauge during the heating of each sample to generate a plurality of measurements of the resistance of the rubber sample, in the form of the measurements of the torque T upon the rotor at peak stress;
   (d) averaging successive measurements of the torque upon the rotor at peak stress to generate a plurality of average torque values;
   (e) comparing the average torque values to each other to generate a minimum average torque value $T_{min}$;
   (f) comparing the average torque values to the minimum average torque value to generate a first selected average torque value $T_{int}$ which is approximately a selected amount greater than the minimum average torque value;
   (g) manipulating at least several of the average torque values following the first selected average torque value $T_{int}$, to generate a maximum first derivative value $T_{max}'$ of said average torque values;
   (h) manipulating the average torque values which follow the average torque values corresponding to the maximum first derivative value $T_{max}'$ to generate a selected first derivative value $T_{det}'$ of approximately a selected ratio to the maximum first derivative value;

(i) determining a second selected average torque value $T_{det}$ corresponding to the selected first derivative value $T_{det}'$;

(j) manipulating the average torque values close in time to the second selected torque value $T_{det}$ to generate the second derivative $T_{det}''$ of the average torque values at the second selected torque value $T_{det}$;

calculating a predicted maximum torque Y, and thereby a predicted maximum resistance of the rubber sample, according to the formula $$Y = T_{det} + (T_{det}'(1 - T_{det}'/(T_{det}'' \times K)))/2$$

where K is an acceleration scale factor;

and terminating the heating of each sample after the calculation of the predicted maximum torque Y.

14. A process as in claim 15 in which the selected amount by which the first selected average torque value $T_{int}$ exceeds the minimum average torque value $T_{min}$ is approximately one deci-newton-meter.

15. A process as in claim 15 in which the selected ratio of the selected first derivative value $T_{det}'$ to the maximum $T_{max}'$ is approximately 0.25, and K is approximately 0.45.

16. A process of curing and testing a rubber sample comprising:

(a) heating the rubber sample;
(b) making at least a plurality of measurements of the resistances of the rubber sample during heating, to generate a plurality of resistance measurements;
(c) determining, from the resistance measurements, a minimum resistance $S_{min}$;
(d) determining, following $S_{min}$ and from the resistance measurements, the maximum rate $S_{max}'$ of change of the resistance;
(e) determining, from the resistance measurements, the occurence of a rate of change of the resistance $S_{det}'$ of approximately a selected ratio to the maximum rate of change $S_{max}'$;
(f) determining, from the resistance measurements, the resistance $S_{det}$ at which the rate of change equals $S_{det}'$;
(g) determining, from the resistance measurements, the rate of change $S_{det}''$ of the rate of change of the resistance in proximity to the rate of change $S_{det}'$;
(h) predicting an expected maximum resistance Y of the rubber sample during the heating according to a relationship relating Y, $S_{det}$, $S_{det}'$ and $S_{det}''$; and
(i) terminating the test and cure based on the expected maximum resistance Y.

* * * * *